United States Patent [19]

Thomas

[11] Patent Number: 5,084,251
[45] Date of Patent: Jan. 28, 1992

[54] INSTRUMENT STERILIZATION CASSETTE

[76] Inventor: Akatheputhethu C. Thomas, 10516 Cradlerock Dr., Dallas, Tex. 75217

[21] Appl. No.: 427,450

[22] Filed: Oct. 26, 1989

[51] Int. Cl.⁵ ............................................. A61L 9/12
[52] U.S. Cl. ................................. 422/300; 206/557; 220/346; 422/102; 422/104
[58] Field of Search ............ 422/102, 104, 297, 300, 422/310; 206/438, 439, 370, 557; 215/236; 220/346; 239/59

[56] References Cited

U.S. PATENT DOCUMENTS

| | | | |
|---|---|---|---|
| 2,247,600 | 7/1941 | Brennan et al. | 239/59 X |
| 2,783,084 | 2/1957 | Paxton | 239/59 |
| 4,253,870 | 6/1985 | Spector | 239/59 X |
| 4,257,537 | 3/1987 | Uhlig | 220/346 X |
| 4,783,321 | 11/1988 | Spence | 206/439 X |
| 4,915,913 | 4/1990 | Williams et al. | 422/297 X |
| 4,959,199 | 9/1990 | Brewer | 422/300 |
| 4,978,510 | 12/1990 | Smith | 422/297 X |

*Primary Examiner*—Robert J. Warden
*Assistant Examiner*—Amalia Santiago
*Attorney, Agent, or Firm*—Hubbard, Thurman, Tucker & Harris

[57] ABSTRACT

An instrument sterilization cassette, into which instruments to be sterilized may be placed on an internal support rack structure, has a housing defined by an open-topped base portion to which a lid portion is pivotally secured. Spaced series of flow openings are formed through the top and bottom side walls of the lid and base portions and permit a vertical throughflow of sterilizing fluid through the cassette, and across the instruments supported therein, when the lid portion is closed. An external latch structure is operative to releasably hold the lid portion closed, and is secured to perforated upper and lower plates slidably supported on the inner side surfaces of the top and bottom side walls of the cassette. By pulling the latch structure outwardly from the housing, the plate members are slidably moved in the same direction and their openings are moved into registry with the top and bottom side wall flow openings to permit a throughflow of sterilizing fluid through the cassette. By pushing the latch structure toward the housing, the plate members are slidably moved in a manner causing them to block the flow openings and close the cassette housing to protect the sterilized instruments from airborne contamination until the cassette is later opened when the sterilized instruments are to be used. A resilient locking mechanism within the housing releasably holds one of the plate members in its blocking position to inhibit undesired outward movement of the latch structure and a corresponding unblocking of the flow openings.

15 Claims, 2 Drawing Sheets

INSTRUMENT STERILIZATION CASSETTE

BACKGROUND OF THE INVENTION

The present invention relates generally to instrument sterilization apparatus and methods and, in a preferred embodiment thereof, more particularly provides an improved cassette device for use in sterilizing dental and surgical instruments or the like.

Dental and surgical instruments or the like are conventionally sterilized by placing them in a box-like storage structure typically referred to as a "cassette". The cassette, with the instruments to be sterilized suitably supported therein, is placed in an appropriate sterilizer and subjected to a flow of sterilizing fluid such as steam or hot air.

Many currently available cassettes used in the sterilization and storage of dental surgical instruments do not provide for the entry of the sterilizing fluid into the interior of the cassette. Accordingly, the overall instrument sterilization time is undesirably increased. As an alternative to this type of completely enclosed sterilization cassette, various proposals have been made to form the cassette from wire mesh, or other perforated wall structures, thereby permitting substantially unimpeded throughflow of sterilization fluid through the interior of the cassette. However this "open" type of instrument sterilization cassette, though greatly diminishing the total sterilization time for the instruments, carries with it other disadvantages and limitations.

For example, due to its "open" construction, the typical wire mesh cassette rapidly permits the contamination of the sterilized instruments when the cassette is removed from the sterilizing chamber and placed in a storage location. To eliminate this serious limitation in conventional wire mesh cassettes, or in other "open" type cassettes, it has heretofore been necessary to wrap the cassettes, after the instruments to be sterilized have been placed therein, with a suitable gauze material which permits a throughflow of sterilizing fluid, yet is essentially impermeable to airborne contaminants to which the cassette is exposed once it is removed from the sterilizing device and placed in a storage location.

This previous necessity of pre-wrapping the open construction cassette adds to the overall cost of the sterilization process, increases the sterilization time, and presents a rather tedious task which must be performed in conjunction with the sterilization of each batch of instruments. Additionally, the gauze material must be unwrapped from its associated stored cassette, and discarded, when it is desired to use the sterilized instruments positioned in the wrapped cassette.

It can be seen from the foregoing that it would be highly desirable to provide an instrument sterilization cassette of essentially "open" construction, to provide for a substantially unimpeded throughflow through the cassette of sterilizing fluid, which need not be pre-wrapped for subsequent instrument storage purposes.

SUMMARY OF THE INVENTION

In carrying out principles of the present invention, in accordance with a preferred embodiment thereof, an instrument sterilization cassette is provided which comprises a housing including a hollow base portion having a bottom side wall and a upper side opening, and a lid portion having an upper side wall, the lid portion being movable between an open position permitting access to the interior of the base portion through its upper side opening, an a closed position in which the lid portion extends across and covers the base portion upper side opening. First and second series of mutually spaced flow openings are respectively formed through the top and bottom side walls of the housing and are operative to permit a sterilizing fluid to be sequentially flowed into the housing, through the housing and across instruments disposed therein, and out of the housing when the lid portion is in its closed position.

Suitable support means are provided for holding a series of instruments to be sterilized in a mutually spaced relationship within the housing when the lid portion is in its closed position. In a preferred embodiment thereof, such support means include a drop-in support rack structure received within the housing base portion, and a plurality of resilient support strips carried within the lid portion and positioned to engage upper portions of the rack-supported instruments when the lid portion is closed.

First and second series of mutually spaced flow openings are respectively formed through the top and bottom side walls of the housing and are operative to permit a sterilizing fluid to be sequentially flowed into the housing, through the housing and across the instruments supported therein, and out of the housing when the lid portion is closed.

Interengagable latch means are carried by the housing base and lid portions and are operative to releasably hold the lid portion in its closed position. The latch means are movable relative to the housing, when the lid portion is in its closed position, between sterilizing and storage positions.

Closure means, carried by the top and bottom side walls, are operative to block the first and second series of flow openings in response to movement of the latch means to their storage position, and are operative to unblock the first and second series of flow openings in response to movement of the latch means to their sterilizing position. In a preferred embodiment thereof, the closure means include top and bottom plates slidably supported on the interior surfaces of the top and bottom side walls and secured to the latch means for movement therewith between their storage and sterilizing positions. These top and bottom plates have formed therein series of openings which are brought into registry with the flow openings in the top and bottom side walls when the latch means are moved to their sterilizing positions. When the latch means are moved to their storage position, the openings in the top and bottom sliding plates are moved out of registry with the flow opening in the top and bottom side walls so that the top and bottom sliding plates cover and block such flow openings.

To inhibit undesired movement of the latch means from their storage position to their sterilizing position when the cassette is removed from the sterilizing device, locking means are provided within the cassette housing to releasably hold the upper sliding plate in the position to which it is moved when the latch means are moved to their storage position. Since the top and bottom sliding plates are interconnected through the latch means, these locking means also releasably hold the bottom sliding plate in the position to which it is moved when the latch means are moved to their storage position.

Due to the unique provision of the perforated top and bottom sliding plates which are associated with the latch means for movement therewith, the instrument sterilization cassette of the present invention provides the advantages of a conventional wire mesh cassette, or other "open" construction cassettes, without the previous necessity of pre-wrapping the cassette and then unwrapping it to use the sterilized instruments previously positioned therein. With the cassette of the present invention, the instruments to be sterilized are simply positioned within the housing base portion on the rack structure disposed therein, the lid portion is closed and latched, and the latch means are moved to their sterilizing position. The cassette is then placed in the sterilizing apparatus, and a throughflow of sterilizing fluid, such as steam, hot air or chemical vapors, is forced through the cassette flow openings, into and through the cassette and across the instruments supported therein. Due to the availability of this direct throughflow of sterilizing fluid, complete instrument sterilization is effected quite rapidly.

After the sterilization process is completed, the cassette is simply removed from the sterilizing apparatus and the latch means are moved to the storage position in which the top and bottom sliding plates close off the flow openings in the top and bottom side walls of the cassette. The cassette may then be placed in a storage location, the top and bottom sliding plates functioning as barriers against airborne contaminants to protect the sterilized instruments until they are needed. Rapid access to the sterilized instruments is provided simply by releasing the latch means and opening the cassette.

DETAILED DESCRIPTION

As illustrated in FIGS. 1-3A, the present invention provides an improved "flow-through" cassette device 10 utilized to rapidly and efficiently sterilize dental and surgical instruments 12 or the like (FIG. 2) without the previous necessity of pre-wrapping the cassette prior to sterilization of the instruments, and then unwrapping the cassette to remove the sterilized instruments therefrom.

Figure 1:
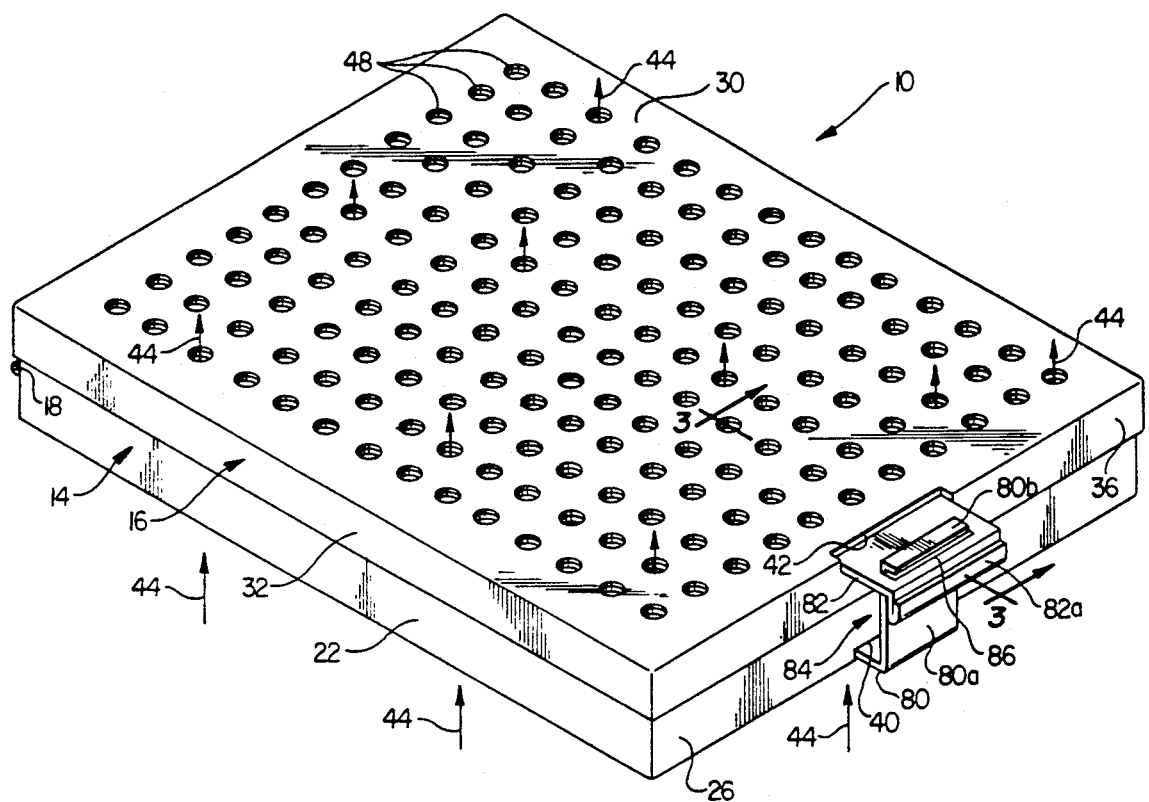
FIG. 1 is a perspective view of an instrument sterilization cassette embodying principles of the present invention, the cassette being illustrated in its closed position.
Figure 2:
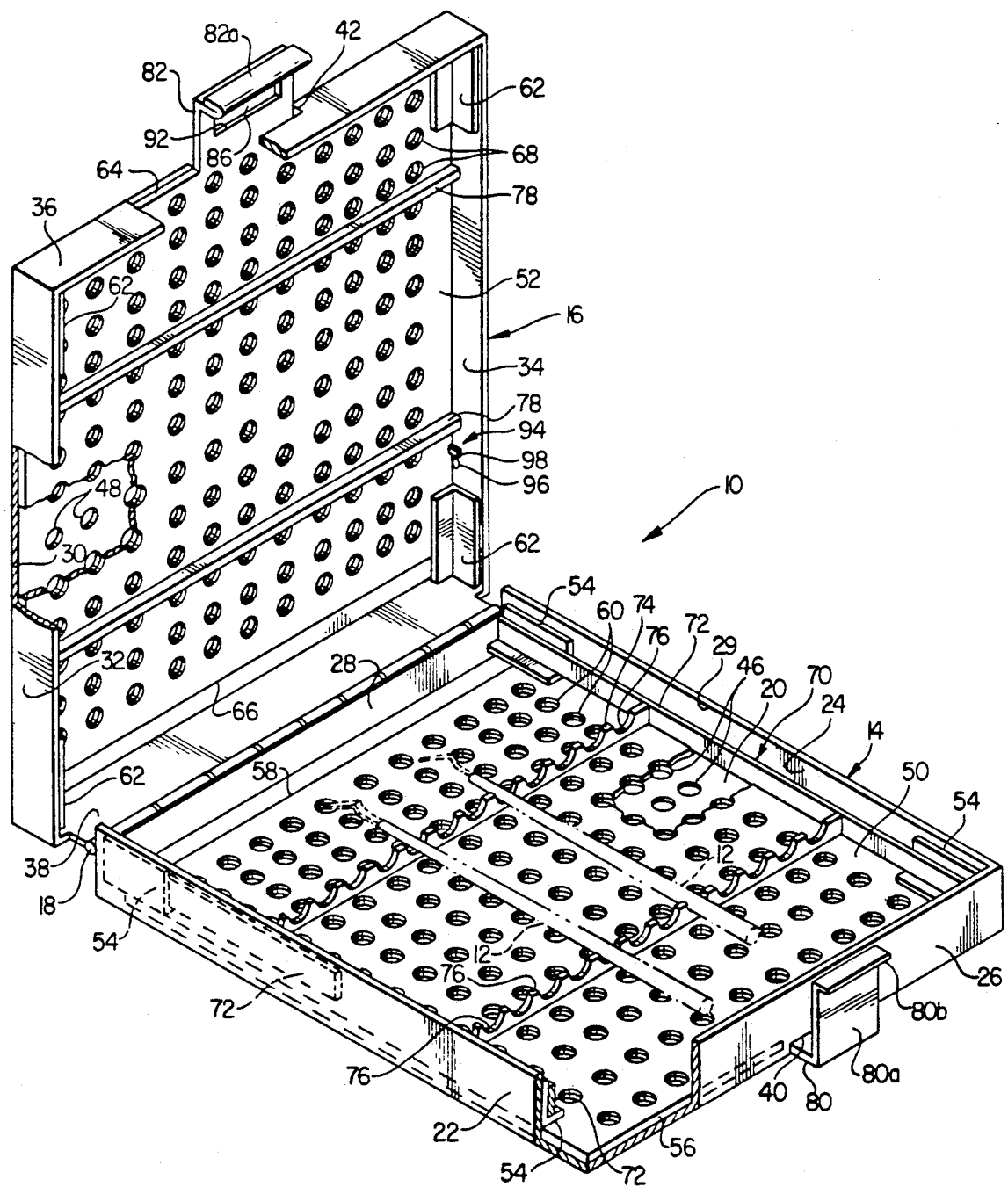
FIG. 2 is a partially cut away perspective view of the cassette in an open position thereof.

The cassette 10 includes a generally rectangular housing formed from stainless steel or another suitable material, and including a base portion 14 and a lid portion 16 pivotally secured to the base portion, as by a hinge structure 18, for movement between a closed position illustrated in FIGS. 1 and an open position illustrated in FIG. 2. Base portion 14 has a bottom side wall 20 from which left and right side walls 22 and 24, and front and rear end walls 26 and 28, upwardly project, and a top side opening 29. Lid portion 16 has a top side wall 30 from whose periphery left and right side walls 32 and 34, and front and rear end walls 36 and 38, downwardly project, the rear end walls 28, 38 being pivotally intersecured by the hinge structure 18. For purposes later described, elongated central slots 40 and 42 are respectively formed through the front end walls 26 and 36 adjacent their junctures with the bottom and top side walls 20 and 30.

To provide for a direct vertical flow of a sterilizing fluid 44 (FIG. 1) through the cassette 10 across the instruments 12 positioned therein, in a manner subsequently described, with the cassette horizontally disposed within a sterilization chamber (not shown) and the lid portion 16 in its closed position, a mutually spaced series of circular flow openings 46 is formed through the bottom side wall 20, and a mutually spaced series of circular flow openings 48 is formed through the bottom side wall 30. The cassette 10 is thus basically of an "open" construction which permits the instruments 12 to be rapidly sterilized by the direct vertical throughflow of the sterilizing fluid 44.

According to an important aspect of the present invention, the circular flow openings 46 and 48 may be selectively blocked and unblocked by a pair of elongated rectangular metal plates 50 and 52. The bottom plate 50 is captively retained on the upper side surface of the bottom side wall 20, for sliding front-to-rear movement relative thereto, by four generally L-shaped metal retaining tab members 54, two of which are secured to the base portion side wall 22, and two of which are secured to the base portion side wall 24 as illustrated in FIG. 2. The distance between the front and rear end edges 56 and 58 of plate 50 is shorter than the distance between the base portion front and rear end walls 26 and 28 so that the plate 50 ma be slidingly moved relative to the bottom side wall 20 between a forward position (FIG. 2) in which the end edge 56 of the plate 50 abuts the front end wall 26, and a rear position in which the rear end edge 58 of the plate 50 abuts the rear end wall 28 of the base portion 14.

Figure 3:
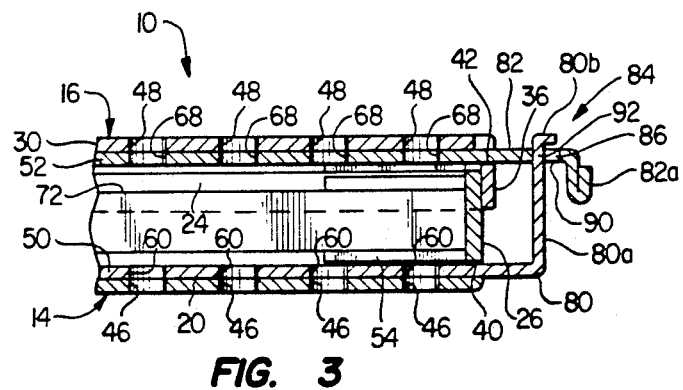
FIGS. 3 and 3A are enlarged scale partial cross-sectional views through the cassette, taken along line 3—3 of FIG. 1, and illustrate the operation of a movable latch portion of the cassette.

For purposes later described, a mutually spaced series of circular openings 60, of the same size and spacing as the flow openings 46 in the bottom side wall 20, is formed through the bottom plate 50. These openings 60 are positioned on the bottom plate 50 so that when it is moved to its forward position its openings 60 are in registry with the flow openings 46 as illustrated in FIG. 3. Conversely, when the bottom plate 50 is moved to its rear position, its openings 60 are moved out of registry with the flow openings 46 in the bottom side wall 20 so that the plate 50 completely blocks the flow openings 46.

The top plate 52 is captively retained on the bottom side surface of the top side wall 30, for front-to-rear sliding movement relative thereto, by four generally L-shaped retaining tab members 62 (FIG. 2), two of which are secured to the left side wall 32 of the lid portion 16, and two of which are secured to the right side wall 34 of the lid portion. The distance between the front and rear end edges 64 and 66 of the top plate 52 is less than the distance between the front and rear end walls 36 and 38 of the lid portion 16. Accordingly, the top plate 52 may be slidingly moved between a forward position (FIG. 2) in which front end edge 64 abuts the front end wall 36 of the lid portion 16, and a rear position in which the rear end edge 66 of the top plate 52 abuts the rear end wall 38 of the lid portion.

Figure 3A:
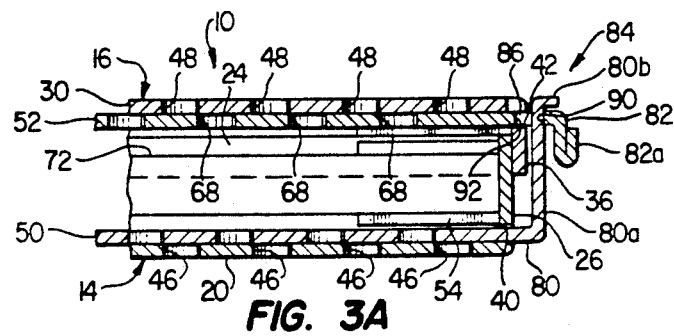

A mutually spaced series of circular openings 68 is formed through the top plate 52, the spacing and size of such openings 68 being identical to the size and spacing of the flow openings 48 formed through the top side wall 30 of the lid portion 16. The circular openings 68 are also positioned on the top plate 52 so that when the top plate is moved to its forward position, its openings 68 are brought into registry with the flow openings 48 in the top side wall 30 as illustrated in FIG. 3. Conversely, when the top plate 52 is moved to its rear position, its openings 68 are moved out of registry with the flow openings 48, and the top plate covers and blocks the flow openings 48 as illustrated in FIG. 3A.

The illustrated instruments 12 are operatively supported within the housing base portion 14, in a mutually spaced orientation relative to each other and relative to the top and bottom side walls 20 and 30, by a drop-in support rack structure 70 which includes a pair of elongated metal rail members 72 which extend lengthwise within the housing base portion 14 and rest upon the retaining tab members 54 as illustrated in FIG. 2. A spaced pair of transverse support members 74, having notches 76 formed therein for receiving the instruments 12, are secured at their opposite ends to the rails 72 and are positioned closely adjacent the upper side surface of the lower sliding plate 50. To securely hold the instruments 12 within the notches 76, a spaced pair of retaining bars 78, formed from a suitable resilient material such as rubber or neoprene, are secured to the upper sliding plate 52 and are positioned to extend along and engage the upper edges of the transverse support members 74 when the lid portion 16 is moved to its closed position.

The bottom and to sliding plates 50 and 52 have formed thereon front end tab portions 80 and 82 which slidably extend outwardly through the front end wall slots 40 and 42 of the base and lid portions 14 and 16, respectively. As will now be described, these tabs 80, 82 define interengagable latch means 84 (FIG. 1) which are operative to releasably hold the housing lid portion 16 in its closed position. The lower tab 80 has an upturned portion $80_a$ with a forwardly bent upper end $80_b$. Tab 82 has an elongated, transverse slot 86 formed therein, and a downturned outer end portion 88. Slot 86 has front and rear side surfaces 90 and 92.

As illustrated, with the housing lid portion 16 in its closed position, the bottom tab portion $80_a$ extendes upwardly through the upper tab slot 86. With the sliding plates 50, 52 in their forward positions (FIG. 3), the outer end portion $82_a$ of the top tab 82 may be grasped and lifted to pivot the lid portion 16 to its open position, the slot 86 been positioned to permit downward passage therethrough of the upper end portion $80_b$ of the lower tab 80. However, with the sliding plates 50, 52 in their rear positions (FIG. 3A), the forwardly bent upper end portion $80_b$ of the lower tab 80 overlies a front end portion of the upper tab 82 and prevents the lid portion 16 from being opened.

By comparing FIGS. 3 and 3A, it can be seen that the latch means 84, defined by the tabs 80 and 82, may be selectively moved in a horizontal direction relative to the cassette housing between a rightwardly extended sterilizing position (FIG. 3) and a leftwardly retracted storage position (FIG. 3A). With the latch means 84 in their sterilizing position, the circular openings 60 and 68 formed in the bottom and top sliding plates 50, 52 are in registry with the flow openings 46, 48 respectively formed in the bottom and top side walls 20, 30 of the housing. With the latch means 84 in their storage position, the bottom and top sliding plates 50, 52 respectively block the lower and upper housing flow openings 46, 48.

The latch means 84 are moved from their sterilizing position (FIG. 3) to their storage position (FIG. 3A) simply by grasping the upper tab portion $82_a$ and pushing it inwardly toward the lid portion front end wall 36. During an initial inward movement of the upper tab 82, the upper plate 52 is leftwardly moved toward its rear position. Upon further leftward movement of the upper tab 82, the front side edge 90 of the slot 86 is brought into engagement with the upstanding lower tab portion $80_a$ and the lower plate 50 is then also moved leftwardly. When the tab portion $80_a$ reaches its fully retracted position (FIG. 3A), both of the plates 50 and 52 have been moved to their rear positions within the housing, and the flow openings 46, 48 are blocked by the plates 50, 52.

To move the latch means 84 from their storage position to their sterilizing position, the upper tab portion $82_a$ is simply grasped and pulled rightwardly. During and initial portion of this rightward movement of the tab portion $82_a$, the upper sliding plate 52 is moved rightwardly. When the rear side edge portion 92 of the tab slot 86 engages the lower tab portion $80_a$ during the balance of the outward movement of the tab portion $82_a$, the lower plate 50 is also moved rightwardly until both of the plates 50, 52 are moved to their forward positions in which the plate openings 60 and 68 are again moved into registry with the lower and upper flow openings 46, 48.

It can thus be seen that to use the cassette 10 the latch means are moved outwardly to their sterilizing position, the lid portion 16 is opened, the instruments 12 are supported within the support member notches 76, and the lid portion 16 is closed to permit the vertical throughflow of sterilizing fluid 44 through the flow openings 46, 48 of the cassette 10 when it is positioned within a sterilizing chamber.

When the instruments are completely sterilized, the cassette 10 is simply removed from the sterilization chamber, and the latch means 84 are pushed leftwardly to their storage orientation in which the flow openings 64, 48 are respectively blocked by the sliding plates 50, 52 and the latch means prevent opening of the housing lid portion 16. The now closed cassette may be moved to a storage location to await the use of the sterilized instruments 12.

Because of the unique use of the sliding perforated plates 50 and 52, there is simply no need to pre-wrap the cassette 10 with a protective gauze material prior to sterilizing the instruments 12, and there is no need to subsequently unwrap the cassette to gain access to the sterilized instruments therein. All that it necessary is to pull the latch means 84 rightwardly to their sterilizing position and swing the lid portion 16 upwardly to its open position.

To inhibit unintentional movement of the latch means 84 from their storage position to their sterilizing position when the sterilized instruments 12 are being stored within the cassette 10, locking means 94 are provided within the lid portion 16 and are operative to releasably hold the upper sliding plate 52 in its rear position. The locking means 94 include a small hemispherical projection 96 formed on the inner side surface of the right lid portion side wall 34, and a resilient tab member 98 secured to and projecting downwardly from the upper sliding plate 52. When the latch means 84 are pushed inwardly to their storage position, the resilient tab member 98 is inwardly deflected upon engaging the projection 96, and is moved rearwardly past the projection as the upper plate 52 moves to its rear position within the lid portion 16. Subsequent forward movement of the upper plate 52 is inhibited by the engagement of the resilient tab member 98 with the projection 96. Since the upper sliding plate 52 is interlocked with the lower sliding plate 50 via the latch means 84 as previously described, the locking means 94 also operate to inhibit undesired forward movement of the bottom sliding 50 from its rear position, thereby releasably maintaining the sliding plates 50, 52 in their storage orientations. When it is desired to open the cassette 10 by rightwardly pulling the latch means 84, the tab member 98 is inwardly deflected and then pulled forwardly past the projection 96.

The foregoing detailed description is to be clearly understood as being giving by way of illustration and example and only, the spirit and scope of the present invention being solely by the appended claims.

What is claimed is:

1. An instrument sterilization cassette comprising:
   a housing within which instruments to be sterilized may be placed, said housing including;
   a hollow base portion having an access opening therein through which instruments may be placed in and removed from said base portion,
   a lid portion movable between an open position permitting access to the interior of said base portion through said access opening, and a closed position in which said lid portion extends across and covers said access opening, and
   first and second spaced apart walls each having a series of mutually spaced flow openings formed therethrough, said flow openings being operative, with said lid portion in its closed position, to permit a sterilizing fluid to be sequentially flowed into said housing through one of said series of mutually spaced flow openings, through the interior of said housing across instruments disposed therein, and out of said housing through the other of said series of mutually spaced flow openings; and
   closure plate means carried by said first and second spaced apart walls for sliding movement relative thereto between a storage position in which said closure plate means block each of said series of mutually spaced flow openings, and a sterilizing position in which said closure plate means unblock each of said series of mutually spaced flow openings.

2. The instrument sterilization cassette of claim 1 wherein:
   said closure plate means have formed therein a mutually spaced series of openings which are brought into registry with said series of mutually spaced flow openings when said closure plate means are moved to their sterilizing position.

3. The instrument sterilization cassette of claim 2 further comprising:
   means positioned externally of said housing for moving said closure plate means to a selected one of said storage and sterilizing positions thereof.

4. The instrument sterilization cassette of claim 3 wherein:
   said closure plate means include a first perforated plate member slidably carried by said first wall, and a second perforated plate member slidably carried by said second wall, and
   said means for moving said closure plate means include latch means, secured to said first and second plate members for movement therewith, for releasably holding said lid portion in its closed position.

5. The instrument sterilization cassette of claim 1 further comprising:
   locking means, disposed within said housing, for releasably holding said closure plate means in their storage position.

6. The instrument sterilization cassette of claim 1 further comprising:
   support means, disposed within said housing, for supporting instruments to be sterilized in a mutually spaced relationship with each other, and with said first and second walls, when said lid portion is in its closed position.

7. An instrument sterilization cassette comprising:
   a housing within which instruments to be sterilized may be placed, said housing including:
   a hollow base portion having a bottom side wall and an upper side opening, and
   a lid portion having an upper side wall, said lid portion being movable between an open position permitting access to the interior of said base portion through said upper side opening, and a closed position in which said lid portion extends across and covers said upper side opening of said base portion;
   first and second series of mutually spaced flow openings respectively formed through said to and bottom side walls and operative to permit a sterilizing fluid to be sequentially flowed into said housing, through said housing and across instruments disposed therein, and out of said housing when said lid portion is in its closed position;
   interengageageable latch means, carried by said base and lid portions, for releasably holding said lid portion in its closed position,
   said latch means being movable relative to said housing, when said lid portion is in its closed position, between first and second positions; and
   closure means carried by said upper and bottom side walls, said closure means being operative to block said first and second series of flow openings in response to movement of said latch means to said first position thereof, and operative to unblock said first and second series of flow openings in response to movement of said latch means to said second position thereof.

8. The instrument sterilization cassette of claim 7 further comprising:
   support means, disposed within said housing, for supporting instruments to be sterilized in a mutually spaced relationship with each other, and with said bottom and upper side walls, when said lid portion is in its closed position.

9. The instrument sterilization cassette of claim 7 wherein:
   said closure means include first and second plate members fixedly secured to said latch means for movement thereby and slidably carried by said upper and bottom side walls, respectively, for movement relative thereto, said first and second plate members each having a series of mutually spaced openings formed therethrough and positioned to be respectively brought into registry with said first and second series of mutually spaced flow openings in response to movement of said latch means to said first position thereof, and to be moved out of registry with said first and second series of flow openings when said latch means are moved to said second position thereof.

10. The instrument sterilization cassette of claim 7 wherein:
   said closure means are slidably carried by said housing and are secured to said latch means for movement therewith between a first position in which said closure means block said first and second series of flow openings, and a second position in which said closure means unblock said first and second series of flow openings, and
   said instrument sterilization cassette further comprises cooperating locking means on said housing and said closure means for releasably holding said closure means in said first position thereof.

11. An instrument sterilization cassette comprising:
   a housing within which instruments to be sterlized may be placed, said housing including:
      a generally rectangular hollow base portion having a bottom side wall with a periphery from which front and rear end walls, and a pair of opposite side walls, upwardly project, a top side opening, and a first slot formed centrally through said front end wall,
      a generally rectangular lid portion having an upper side wall with a periphery from which front and rear end walls, and a pair of opposite side walls, downwardly project, and a second slot formed centrally through said front end wall of said lid portion,
      a first series of mutually spaced sterilizing fluid flow openings formed through said bottom side wall,
      a second series of mutually spaced sterilizing fluid flow openings formed through said upper side wall, and
      a hinge structure pivotally interconnecting said rear end walls of said base portion and said lid portion and permitting said lid portion to be moved relative to said base portion between an open position permitting access to the interior of said base portion through said access opening, and a closed position in which said lid portion extends across and covers said access opening;
   a first plate member supported on the interior side surface of said bottom side wall for sliding front-to-rear movement relative thereto between first and second positions, said first plate member having a series of mutually spaced openings formed therethrough and a front tab portion extending outwardly through said first slot for front-to-rear movement therethrough,
   said first plate member in said first position thereof blocking said first series of sterilizing fluid flow openings, said mutually spaced openings in said first plate member being positioned thereon to be brought into registry with said first series of sterilizing fluid flow openings when said first plate member is moved to its second position;
   a second plate member supported on the interior side surface of said upper side wall for sliding front-to-rear movement relative thereto between first and second positions, said second plate member having a series of mutually spaced openings formed therethrough and a front tab portion extending outwardly through said second slot for front-to-rear movement therethrough,
   said second plate member in said first position thereof blocking said second series of sterilizing fluid flow openings, said mutually spaced openings in said second plate member being positioned thereon to be brought into registry with said second series of sterilizing fluid flow openings when said second plate member is moved to its second position; and
   interengageable latch means, positioned externally of said housing and defined by outwardly projecting sections of said front tab portions of said first and second plate members, for releasably holding said lid portion in its closed position,
   said latch means, with said lid portion in its closed position, being movable relative to said housing generally parallel to said first and second plate members to selectively and substantially simultaneously move said first and second members between their first and second positions.

12. The instrument sterilization cassette of claim 11 further comprising:
   cooperative locking means, on an interior portion of said housing and on one of said first and second plate members, for releasably holding said one of said first and second plate members in its first position.

13. The instrument sterilization cassette of claim 12 wherein:
   said cooperative locking means include a projection formed on the inner side of one of said opposite side walls of said lid portion, and a resilient tab member secured to said second plate member and operatively engageable with said projection.

14. The instrument sterilization cassette of claim 11 further comprising:
   support means, disposed within said housing, for supporting instruments to be sterilized in a mutually spaced relationship with each other, and with said upper and bottom side walls, when said lid portion is in its closed position.

15. The instrument sterilization cassette of claim 14 wherein said support means include:
   a plurality of mutually spaced support members removably positioned within said base portion and projecting upwardly from said first plate member, said support members having downwardly extending notches formed therein for receiving portions of instruments to be sterilized, and
   a plurality of elongated, resilient retaining members secured to said second plate member and positioned to be brought downwardly into engagement with said support members when said lid portion is moved to its closed position.

* * * * *

UNITED STATES PATENT AND TRADEMARK OFFICE
CERTIFICATE OF CORRECTION

PATENT NO. : 5,084,251
DATED : January 28, 1992
INVENTOR(S) : Thomas

It is certified that error appears in the above-identified patent and that said Letters Patent is hereby corrected as shown below:

In column 2, line 1, delete the word "an" and add the word --and--.

In column 8, line 25, delete the word "to" and add the word --top--.

In column 8, line 31, delete the word "interengageageable" and add the word --interengageable--.

Signed and Sealed this

Twenty-fifth Day of May, 1993

Attest:

MICHAEL K. KIRK

Attesting Officer

Acting Commissioner of Patents and Trademarks